United States Patent [19]

Lazzara et al.

[11] Patent Number: 4,850,873
[45] Date of Patent: Jul. 25, 1989

[54] PROSTHODONTIC RESTORATION COMPONENTS

[75] Inventors: Richard J. Lazzara, Lake Worth; Keith D. Beaty, West Palm Beach, both of Fla.

[73] Assignee: Implant Innovations, Inc., W. Palm Beach, Fla.

[21] Appl. No.: 178,296

[22] Filed: Apr. 4, 1988

[51] Int. Cl.4 ................................................ A61C 5/06
[52] U.S. Cl. ................................................... 433/220
[58] Field of Search ............... 433/173, 174, 175, 176, 433/218, 219, 220, 221

[56] References Cited

U.S. PATENT DOCUMENTS 4,722,688 2/1988 Lonca ..................................... 433/173
4,744,756 5/1988 Ross ....................................... 433/173

Primary Examiner—Robert Peshock
Attorney, Agent, or Firm—Alfred H. Rosen

[57] ABSTRACT

In a dental post and coping combination in which the coping is a tubular envelope open at one end, a shoulder around the base of the post which has an annular surface on the locus of a first curvilinear surface, and an annular meeting surface around the open end of the coping which is on the locus of a second shallower curvilinear surface cone, so that when the two parts are assembled the two surfaces meet on the locus of a circle that coincides with the larger periphery of at least one of the two surfaces.

9 Claims, 1 Drawing Sheet

PROSTHODONTIC RESTORATION COMPONENTS

This invention relates in general to the field of prosthodontic restoration; more particularly to the combination of an abutment post and a coping for enabling a restorative dentist to provide improved prosthodontic restorations. This invention is an improvement on the post and coping structure shown and described with reference to FIG. 2 in our copending application for U.S. patent Ser. No. 111,868 filed Oct. 23, 1987.

In use, the post of a post and coping combination is fixed in the patient's mouth, an artificial tooth, or crown, is fashioned on the coping, and the coping-and-crown are joined to the post, desirably in a removable manner. The post can be fixed in a dental implant, as is illustrated in our copending application, or it may be supported endodontically, that is, on a root or roots of a lost tooth which have been endodontically prepared to receive it. In the embodiment of the invention that is illustrated and described in the following specification the invention is exemplified as it might be used in connection with a dental implant. In the appended claims, however, the invention is addressed generically, without regard to the underlying structure on which the post may be supported.

The present invention is concerned primarily with the problems of providing hygienically satisfactory and cosmetically pleasing dental restorations. To satisfy the first of these goals the margin between an artificial tooth and its underlying support must be smooth and tight, so that it will not catch an explorer and will seal out moisture and bacteria. To satisfy the second of these goals the same margin should be on the gum line, so that the underlying support structure will not be visible when the restored tooth is in view. The present invention satisfies both of these goals with a post and coping structure that requires no special skill or art from the restorative dentist.

FIG. 2 of our copending application shows the combination of a dental post and a generally tubular coping intended to envelop the post when the two are assembled on a common axis. The post has an annular shoulder disposed around the common axis as a center and the coping has an annular meeting surface which comes to rest on and is supported by the shoulder when the coping is mounted on the post. The present invention is addressed to improve the meeting contact between the shoulder of the post and the meeting surface of the coping.

The present invention provides, in the aforesaid post and coping combination, an improved structure in which, in a preferred embodiment, the meeting surface of the coping lies on the locus of the surface of a first cone the outer aspect of which makes a first angle with a plane perpendicular to the common axis, the support surface of the shoulder lies on the locus of the surface of a second cone the inner aspect of which makes a second angle with the same or a parallel plane, and the second angle is greater than the first angle. In this improved combination first contact between the surface of the shoulder and the meeting surface of the coping will occur on the locus of a circle that coincides with the larger periphery of at least one of the two surfaces. Preferably first contact occurs on the locus of that circle which coincides with the larger periphery of each of the two surfaces.

In another embodiment of the invention the meeting surface of the coping lies on the locus of a first spherical curve, the support surface of the shoulder lies on the locus of a second spherical curve, and the radius of the first curve is larger than the radius of the second curve.

The invention is explained in greater detail in the following description of an embodiment that is illustrated in the drawings, in which.

Figure 1:
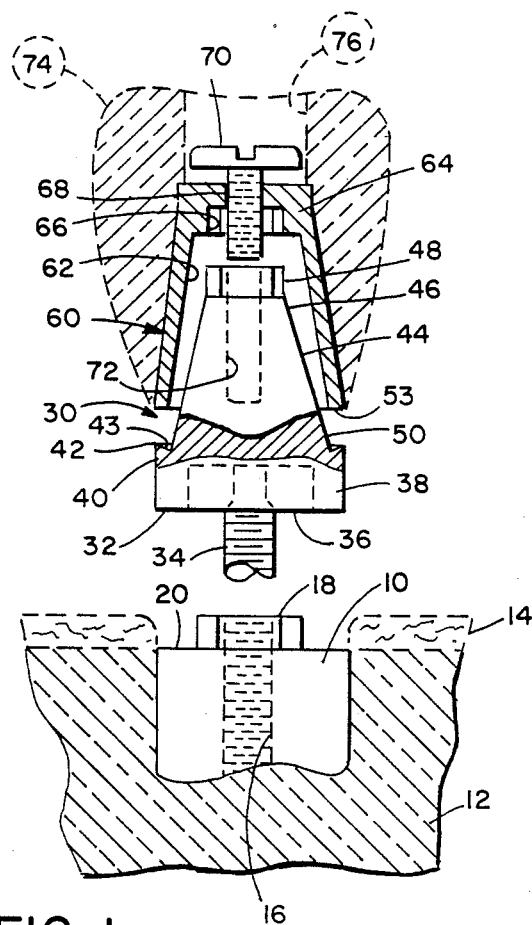
FIG. 1 is an axially-exploded view of a post and a coping.

In FIG. 1 an implant 10 is shown installed in a jawbone 12 covered with gum tissue 14. An internally-threaded bore 16 in the implant opens to the gum through the top 20 of the implant. An abutment post 30 has at its first end 32 a screw 34 for engaging in the bore 16 and fixing the post to the implant. A re-entrant cavity 36 in the first end provides room to enclose a fitting 18 on the top 20, and the screw extends out of this cavity from its bottom. A skirt 38 around the cavity has substantially the same outer diameter as the implant 10, and when the post 30 is affixed to the implant the annular surface of the post at its first end 32 mates with the surface at the top 20 of the implant 10. The outer cylindrical surface 40 of the skirt 38 has an axial length which is substantially the same as the thickness of the gum tissue 14, providing a trans-tissue section of the post from which a tapered post section 50 extends supragingivally. The tapering surface 44 of the post section terminates within the locus 42 marking the boundary of the cylindrical surface 40 where the post section meets the trans-tissue section, providing an annular shoulder 43 between the wide end of the post section 50 and the supragingival aspect of the cylindrical surface 40. The surface of this shoulder lies on the locus of the surface of a shallow cone the inner aspect of which makes an angle with a plane transverse to the common axis of the post and coping combination, as will be described with reference to FIG. 2. The post section tapers down to a smaller cross-section at its second end 46, supragingivally more remote from the implant 10. A mount section 48 for the coping 60 is fitted to the second end 46 of the post section.

The coping 60 is a generally cone-shaped hollow body having a flaring section 62 dimensioned to fit over and envelope the post section 50, and at its narrower end 64 a socket section 66 dimensioned to cooperate with the mount section 48. The socket section has a bore 68 through its top for the passage of a bolt 70. The post section has an internally-threaded bore 72 extending through the mount section 48 for receiving the bolt. The coping 60 may be fastened to the post 30 with the bolt 70. The wider part of the flaring section 62 of the coping is terminated in an annular meeting surface 52 which meets the shoulder 43 when the bolt 70 is tightened on the post 30. The surface of the meeting surface 53 lies on the locus of the surface of a shallower cone the outer aspect of which makes another angle with a plane transverse to the common axis of the post and coping combination, as will be described with reference to FIG. 2.

A prosthodontic restoration, represented here in dashed line as a tooth 74, may be fashioned on the coping. A hole 76 may be provided through the top of the tooth giving access to the bolt 70, for both fitting the tooth to the post 30 and removing it for later treatment. In practice the hole would be filled with a suitable dental material (not shown). The improvement of the present invention contemplates that such fitting and removing may be done without losing the hygienic and cosmetic advantages of the invention.

Figure 2:
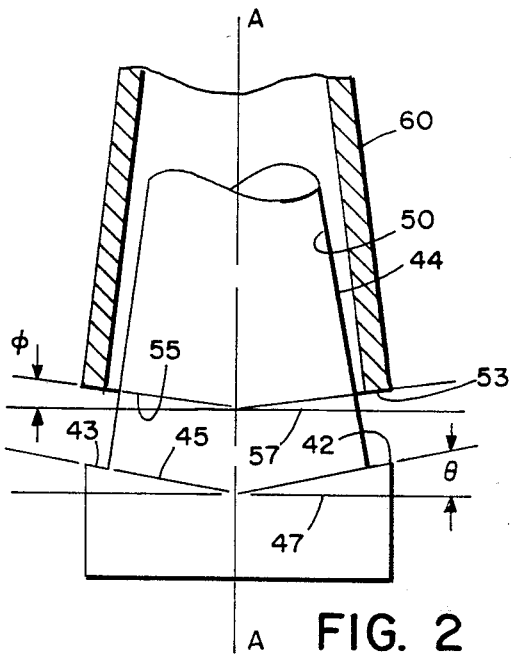
FIG. 2 is an enlarged partial view of FIG. 1.

Referring now to FIG. 2, axis A—A represents the common axis of the post and coping combination. The shoulder 43 provides a support surface for the coping 60, which surface lies on the locus of the surface of a cone 45 the inner aspect of which makes an angle $\theta$ with a plane 47 that is perpendicular to the axis A—A. The annular meeting surface 53 of the coping lies on the locus of the surface of another more open cone 55 the outer aspect of which makes a smaller angle $\phi$ with a plane 57 that is perpendicular to the axis A—A. The two planes 47 and 57 being both perpendicular to the same axis are parallel to each other. The shoulder angle $\theta$ is greater than the meeting surface angle $\phi$. Therefore, when the coping 60 rests on the shoulder 43 first contact between the shoulder surface and the meeting surface 53 will occur on the locus of a circle that coincides with the larger periphery of at least one of those two surfaces. As is shown in FIG. 3, which illustrates a preferred situation, the invention can provide that first contact will occur on the locus of a circle 78 which coincides with the larger periphery of each of those two surfaces.

Figure 3:
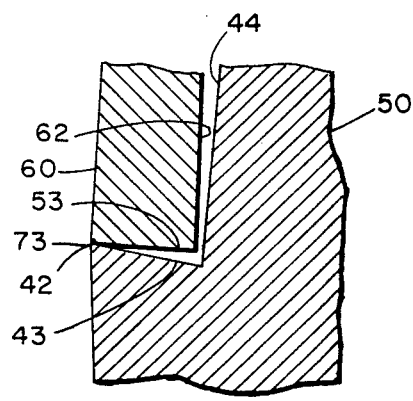
FIG. 3 is a greatly enlarged partial view, in section, showing a preferred meeting-surface relationship of the invention.

Referring to FIG. 3 together with FIG. 1, it will be seen that in the preferred situation when the artificial tooth 74 is fitted to the post 30 the coping will make a smooth tight margin at the meeting circle 78 with the trans-tissue section of the post. That margin will be substantially at the gum line, if the restoring dentist has been careful to choose a post with a trans-tissue section having a thickness which matches the patient's gum thickness. Provided the restored tooth has been fashioned to cover the coping completely to the margin or larger periphery of the meeting surface 53, this will also assure that the tooth will come to the gum line. The bolt 70 will function to seal the outer margin between the tooth and the post in a manner that is both hygienically satisfactory and cosmetically pleasing. Subsequently removing the tooth for dental care or repair and reinstalling it will not deprive the patient of these advantages.

Preferred ranges of angles are, for $\theta$, 5 to 6 degrees, and for $\phi$, 2 to 4 degrees. Generally speaking, the coping may flare at a smaller angle than the taper of the post section 50, so that the coping makes contact with the post only at the meeting surface 53 and in the socket section 66. In the vicinity of the meeting surface the thickness of the wall of the coping is preferable slightly less than the width of the shoulder 43, as appears in FIG. 3, so as to avoid interference with the first contact between the meeting surface and the shoulder on the desired locus; e.g: the margin 78.

First contact between the shoulder surface 43 and the meeting surface 53 will occur on the locus of a circle that coincides with the larger periphery of at least one of these two surfaces for meeting surface angles $\phi$ which are as small as 0 degrees. In that limit, however, the interior space between these two surfaces 43, 53 will be at a larger limit, as is apparent from an examination of FIG. 3. It is preferred to achieve a smaller space between these two surfaces 43,53.

Since the first meeting locus is circular, the coping is urged radially inwardly toward the axis A—A uniformly along this line (e.g.: the margin line 78 in FIG. 3). There is no distortion of the coping 60 along the meeting locus resulting from its assembly on the post 30.

Figure 4:
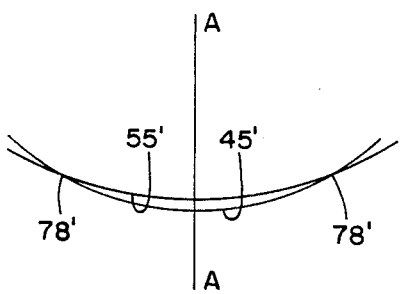
FIG. 4 schematically illustrates another embodiment of the invention.

In FIG. 4 a first spherical curve 45' is the locus for the shoulder 43, and a second spherical curve 55' is the locus for the annular meeting surface 53. As is true of the cones 55, 45 in FIG. 2, the second spherical curve 55' is "more open" than the first spherical curve 45'. That is, the radius of the "more open" curve 55' is larger than the radius of the first curve 45'. The two curves intersect on a circular locus 78', which corresponds to the meeting circle 78 shown in FIG. 3, and which is centered on the axis A—A.

FIG. 4 illustrates that the cones 45,55 and the curves 45',55' are but two examples of curvilinear loci which can satisfy the object of the invention. Generally, these objects will be satisfied if the surfaces of the annular shoulder 43 and the annular meeting surface 53 are shaped to assure that when the coping 60 is fitted to the post 30 the larger periphery of at least one of these two surfaces will make first contact with the other surface, and that preferably the larger peripheries of both surfaces will meet in the same locus.

We claim:

1. The combination of a dental post and a generally tubular coping intended to envelop the post when the two are assembled on a common axis, said post having an annular shoulder disposed around said axis as a center providing an annular support surface extending between an outer periphery and a inner periphery substantially transverse to said axis for receiving an annular end of said coping, said coping having at said end extending between an outer periphery and an inner periphery substantially transverse to said axis an annular meeting surface disposed around said axis as a center, said combination characterized in that said meeting surface lies on the locus of a first curvilinear surface, said support surface lies on the locus of a second curvilinear surface, said curvilinear surfaces are each symmetrical around said axis, and said curvilinear surfaces are so contoured each relative to the other that when said coping is assembled to said post the first contact between said meeting and support surfaces will occur on the locus of a circle that coincides with the larger periphery of at least one of said meeting and support surfaces, and said meeting and support surfaces will be maintained separate from each other at their respective inner peripheries.

2. A combination according to claim 1 in which said first surface is the surface of a first shallow cone the outer aspect of which makes a first angle with a plane perpendicular to said axis, said second surface is the surface of a second shallow cone the inner aspect of which makes a second angle with said plane, and said second angle is greater than said first angle.

3. A combination according to claim 2 in which said first angle is in the range from approximately 2 degrees to approximately 4 degrees, and said second angle is in the range from approximately 5 degrees to approximately 6 degrees.

4. A combination according to claim 2 in which said first angle may be as little as zero degrees.

5. A combination according to claim 1 in which the larger periphery of each of said meeting and support surfaces coincides substantially with the locus of the same circle.

6. A combination according to claim 1 in which said post has at an end remote from said shoulder a threaded bore for receiving a screw, and said coping has at a second end remote from said first-named end a sleeve for passage of a screw, whereby said coping may be screw-tightened on said post so as to clamp said meeting and support surfaces together on said locus of said circle.

7. A combination according to claim 1 in which said post is externally tapered toward said axis progressively away from said support surface and said coping flares internally progressively away from said axis toward said meeting surface, the flare angle of said coping relative to said axis being smaller than the taper angle of said post relative to said axis.

8. A combination according to claim 1 in which said curvilinear surface of said meeting surface is spherical on a first radius, said curvilinear surface of said support surface is spherical on a second radius and said first radius is larger than said second radius.

9. In combination a dental post fitted in a patient's mouth and an artificial tooth supported on said post, said post having at its base an annular shoulder extending between a larger periphery and a smaller periphery substantially at the gum line, said tooth having a cavity for enveloping said post and having at the open periphery of said cavity an annular meeting surface extending between a larger periphery and a smaller periphery of said open periphery, said meeting surface being in contact with said shoulder only at the larger periphery of said meeting surface, the larger periphery of said shoulder and the larger periphery of said meeting surface having like sizes and contours, said shoulder and said meeting surface being shaped to assure that when said tooth is fitted to said post said larger peripheries will meet first, so as to form a tight margin at said gum line, and to maintain a separation between said smaller peripheries of said shoulder and said meeting surface.

* * * * *